United States Patent
Bonacini

(10) Patent No.: US 8,167,956 B2
(45) Date of Patent: May 1, 2012

(54) BRACKET-FIXABLE RUNNING FOOT FOR LOWER LIMB PROSTHESIS

(75) Inventor: Daniele Bonacini, Milan (IT)

(73) Assignee: Roadrunnerfoot Engineering S.R.L., Milan (IT)

(*) Notice: Subject to any disclaimer, the term of this patent is extended or adjusted under 35 U.S.C. 154(b) by 11 days.

(21) Appl. No.: 12/265,787

(22) Filed: Nov. 6, 2008

(65) Prior Publication Data

US 2009/0157197 A1 Jun. 18, 2009

(30) Foreign Application Priority Data

Nov. 9, 2007 (IT) ............................... MI2007A2148

(51) Int. Cl.
*A61F 2/66* (2006.01)
(52) U.S. Cl. .......................................................... 623/55

(58) Field of Classification Search ............... 623/49–55
See application file for complete search history.

(56) References Cited

U.S. PATENT DOCUMENTS 6,514,293 B1 * 2/2003 Jang et al. ........................ 623/55
6,852,132 B1 * 2/2005 Houser et al. .................... 623/52

* cited by examiner

*Primary Examiner* — Bruce E Snow
(74) *Attorney, Agent, or Firm* — Ladas & Parry LLP

(57) ABSTRACT

The prosthetic foot (1) is a lamina of composite material with a characteristic J-shape, fixable by a TT bracket (2) directly to a socket (3) containing the stump, i.e. the residual part of the amputated lower limb, in the case of users with transtibial amputations, or to a TF bracket (2*a*) itself fixable to a mechanical knee (G) fixable to a socket (3*a*), in the case of users with transfemoral amputations. Said socket (3 or 3*a*) has a main axis (5) defined by the loading straight line by which the user, after applying the prosthesis, discharges body weight in the static position, and passing through a point (4) identifying the femoral epicondyle.

12 Claims, 8 Drawing Sheets

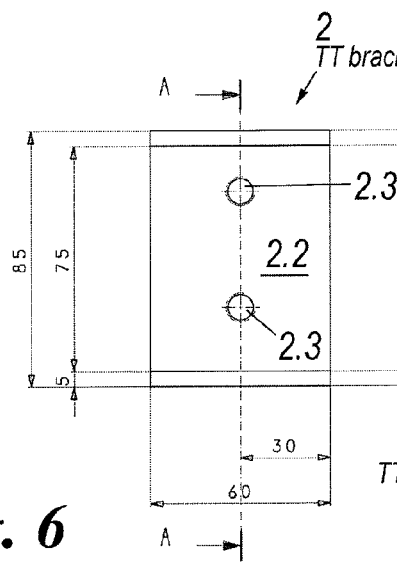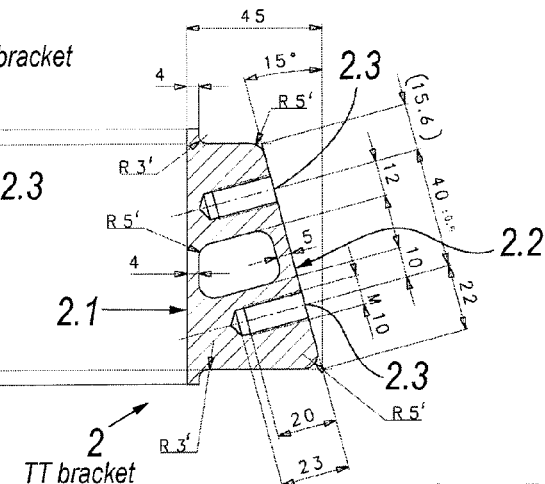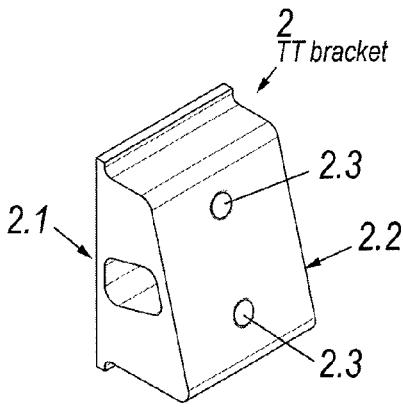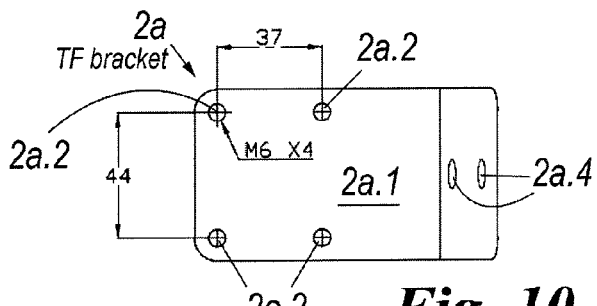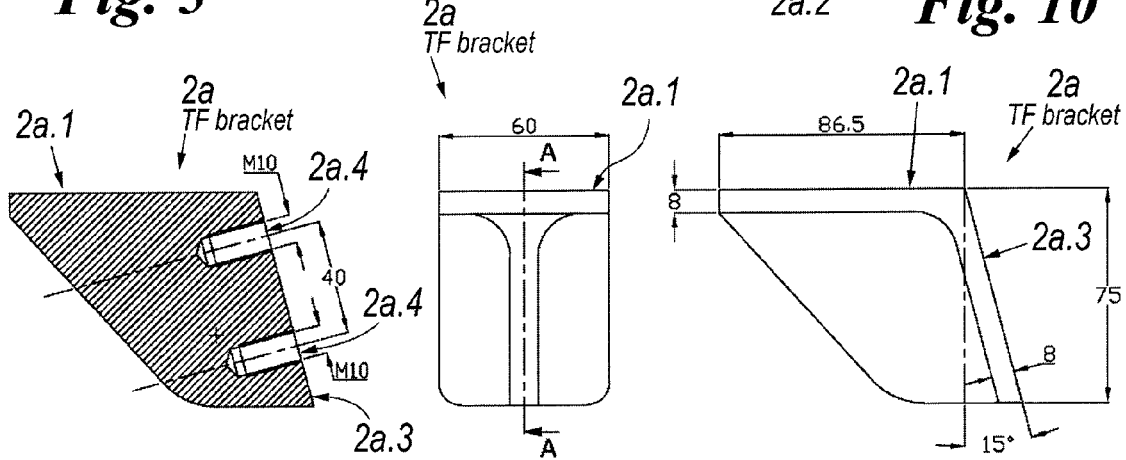
Fig. 6  Fig. 7  Fig. 5  Fig. 10  Fig. 11  Fig. 8  Fig. 9

INCLUDES PRIOR ART

BRACKET-FIXABLE RUNNING FOOT FOR LOWER LIMB PROSTHESIS

The present invention relates to a foot for a lower limb prosthesis which enables a novice user to run while minimizing fatigue, and enables an expert athlete to improve performance in sports competitions.

A prosthetic foot used for running is different from those used for walking, as its functionality is different; running feet are also made of composite material, but always consist of several laminas connected together in such a manner as to perform the functionality of the foot and of the ankle joint. A running foot consists of only one lamina, and hence lacks a lamina which morphologically defines the heel, such as in the human foot: in this respect, this latter lamina is useless for sprinting, i.e. fast running, achieved by bearing on the foot front, and is also useless in a middle-distance race in which the lamina flexes during loading, as in the case of a spring, in such a manner as to increase the contact surface and to form a type of virtual heel.

STATE OF THE ART

The object of the present invention is to enable a new user to commence sporting activities while minimizing the energy consumed and hence fatigue, and to enable a sporting athlete to improve performance, by optimizing the mechanical behaviour of the foot. By analyzing and studying the running of amputated athletes using commercially available feet, it can be noted that during use, in particular during the load application stage, these feet flex by about 30 mm and roll rearwards by about 5° to generate a force in the opposite direction to the advancement direction.

This has given rise to the idea of forming a foot which eliminates the negative component of the force in the advancement direction (Fx) and facilitates running, by also relating the point of maximum peak force in a vertical direction (Fz) and the point of maximum peak advancement force (Figure) to the moment of foot contact with the ground, in which the femur is perpendicular to the ground line, known as mid-stance, such that the user can utilize to a maximum the elastic response generated by the foot, and lastly, but no less important, can establish a better modulus relationship between the vertical force (Fz) and the force in the advancement direction (Fx), such as to enable a wider stride with a knee trajectory closer to the ground.

The object of the present invention is therefore to provide a running foot which during use accurately simulates the functionality of the human foot.

This object is attained by a running foot, the inventive characteristics of which are defined by the accompanying claims.

Figure 1:
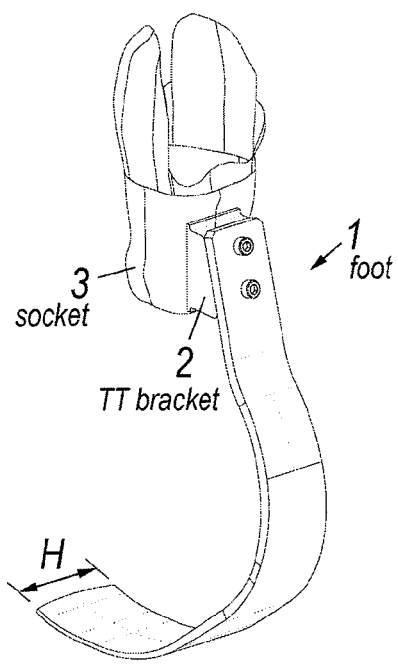
Figure 2:
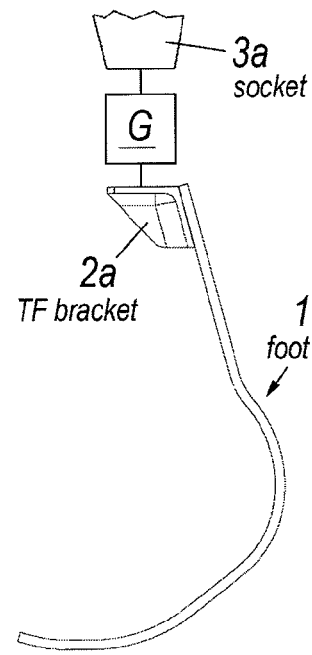
Figure 3:
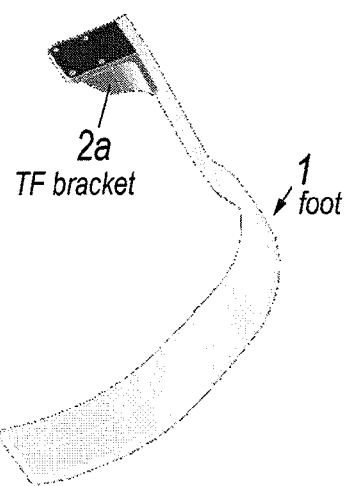
Figure 4:
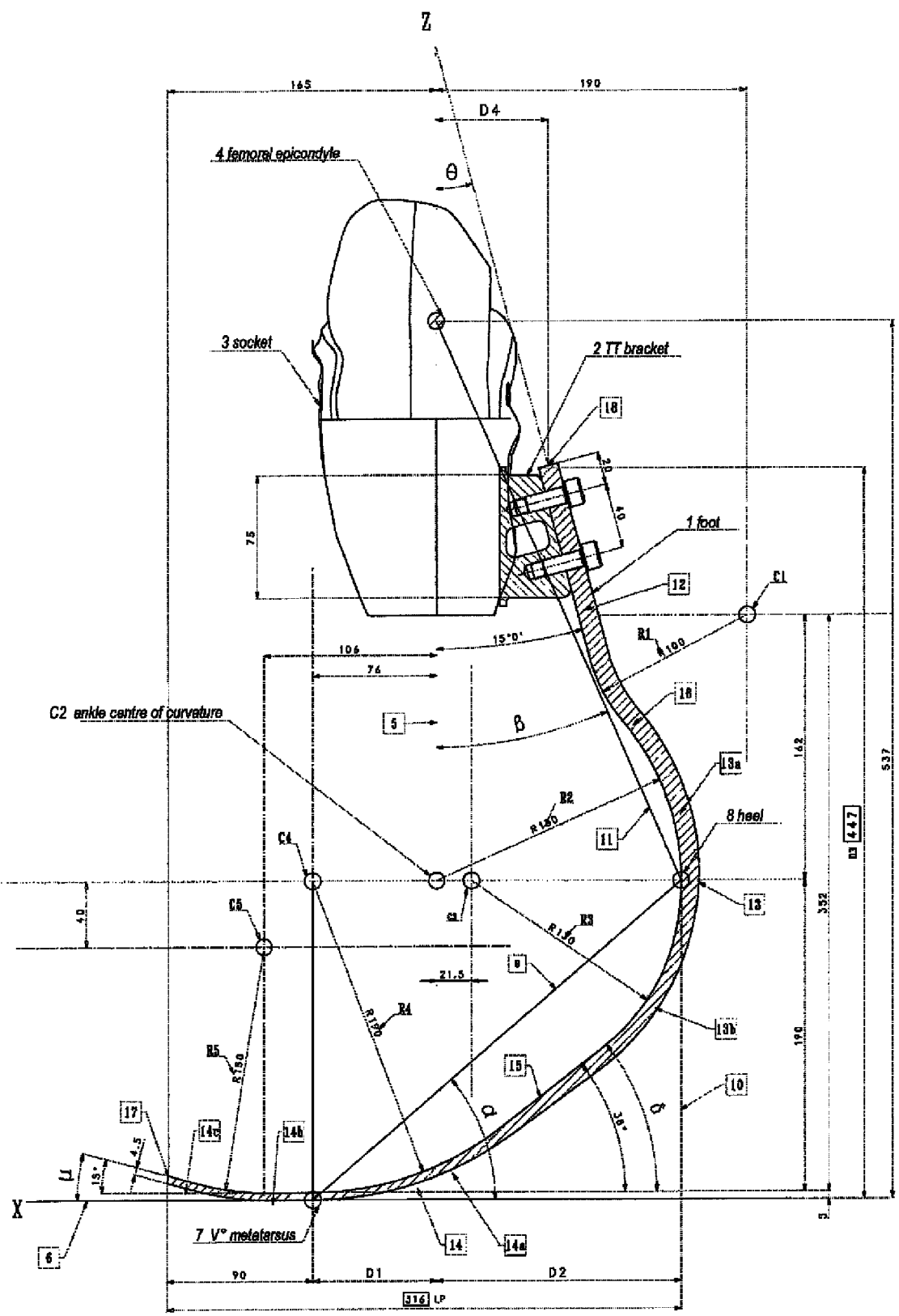
Figure 12:
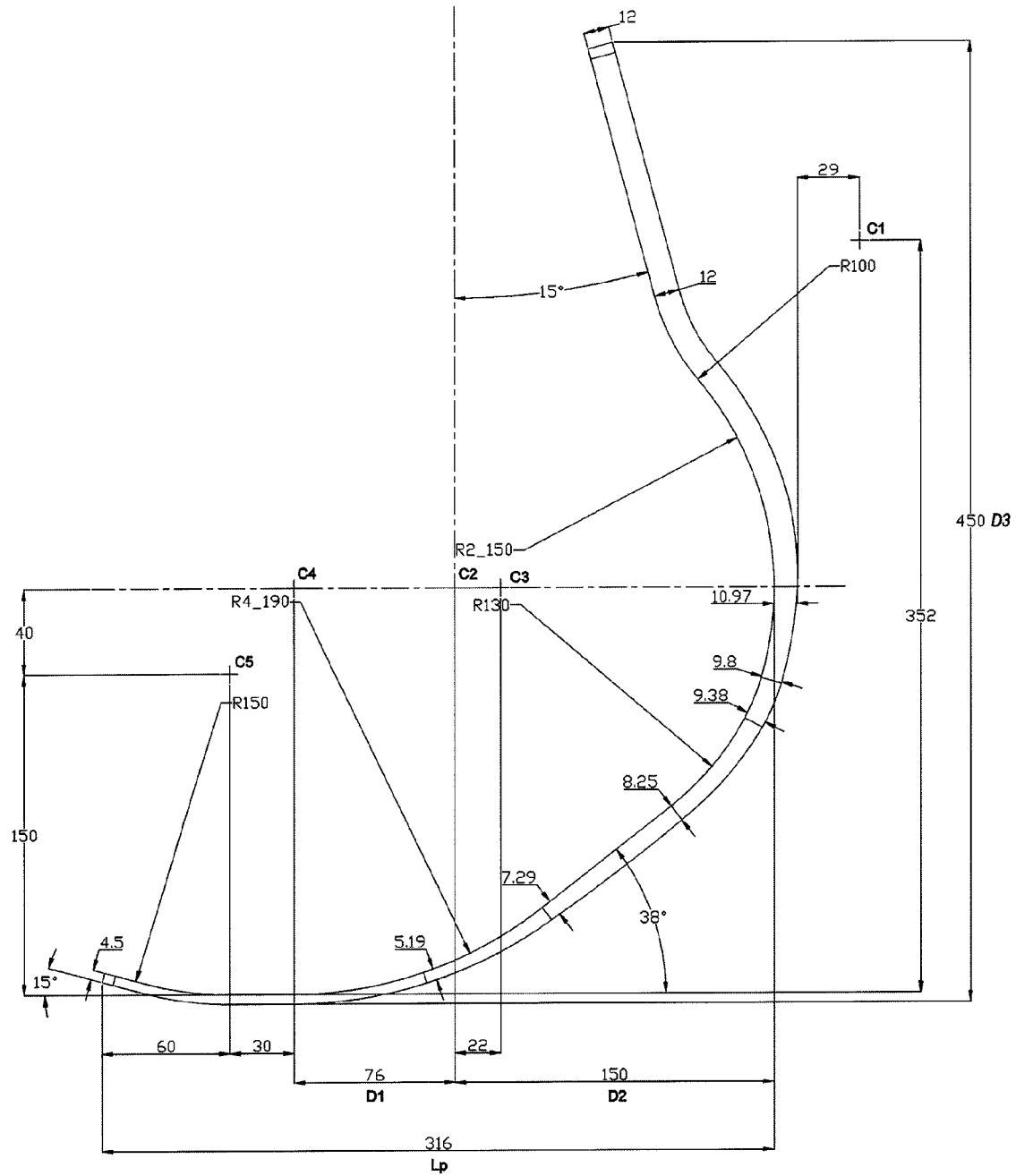
Figure 12A:
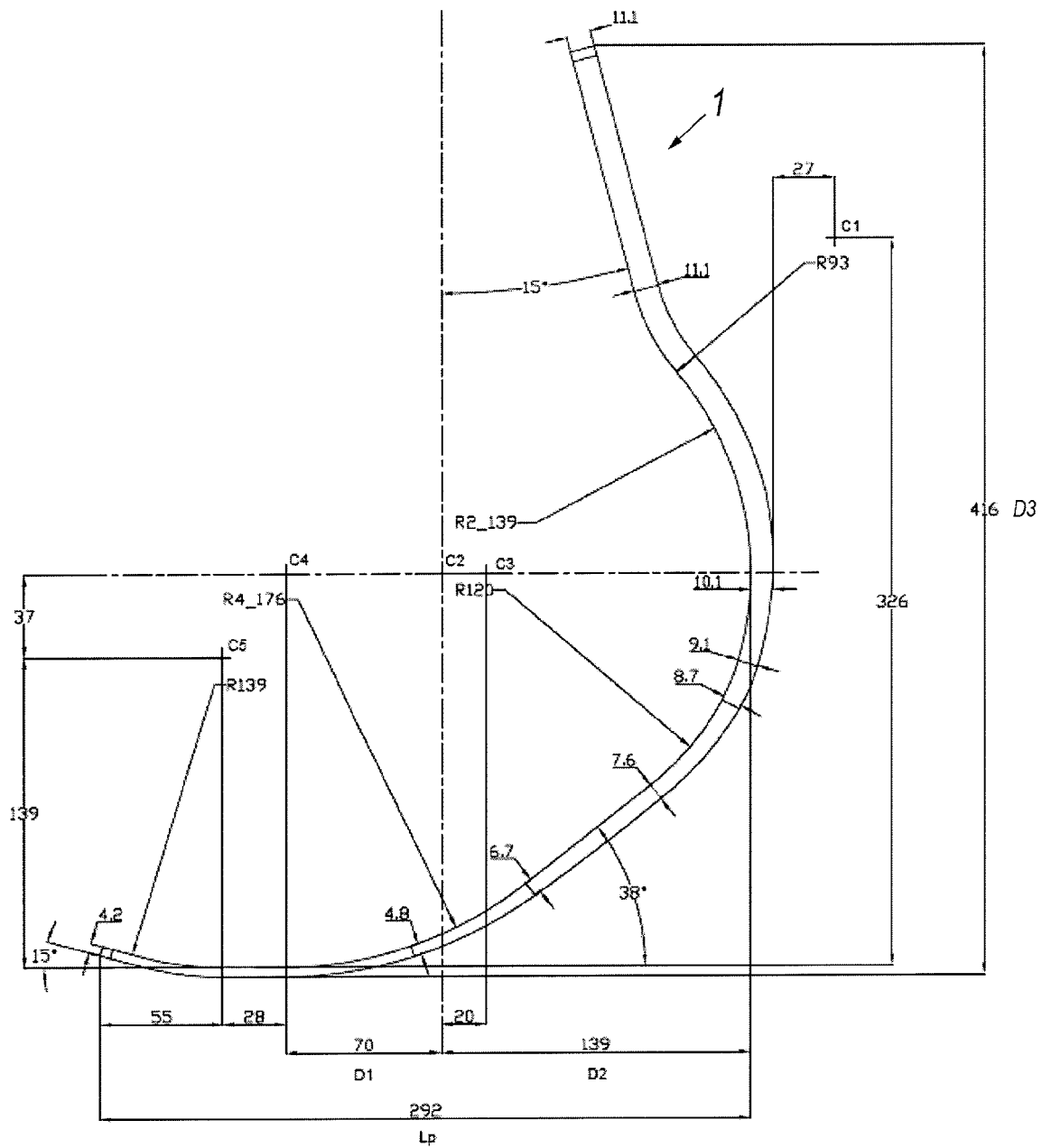
Figure 13:
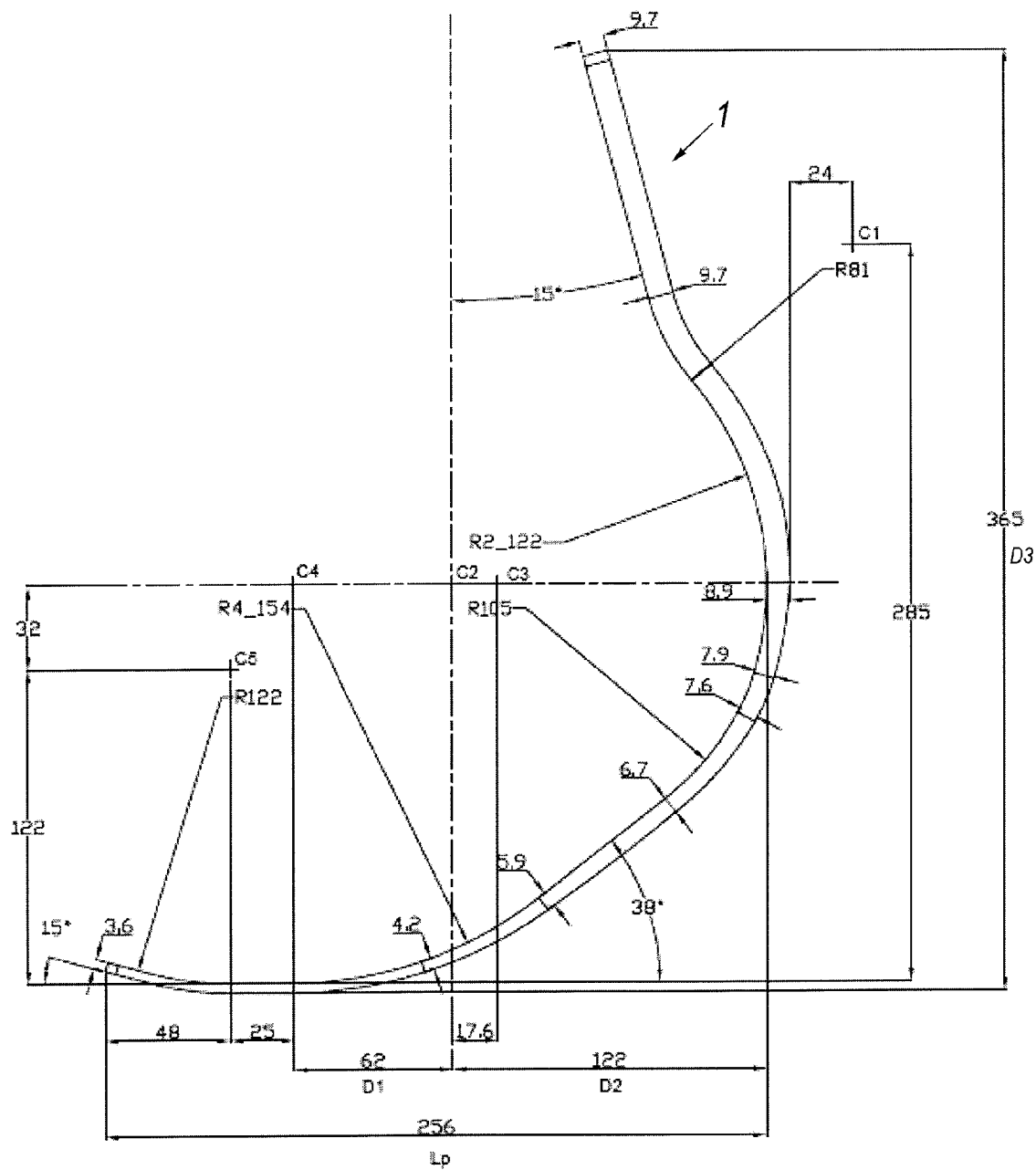
Figure 14:
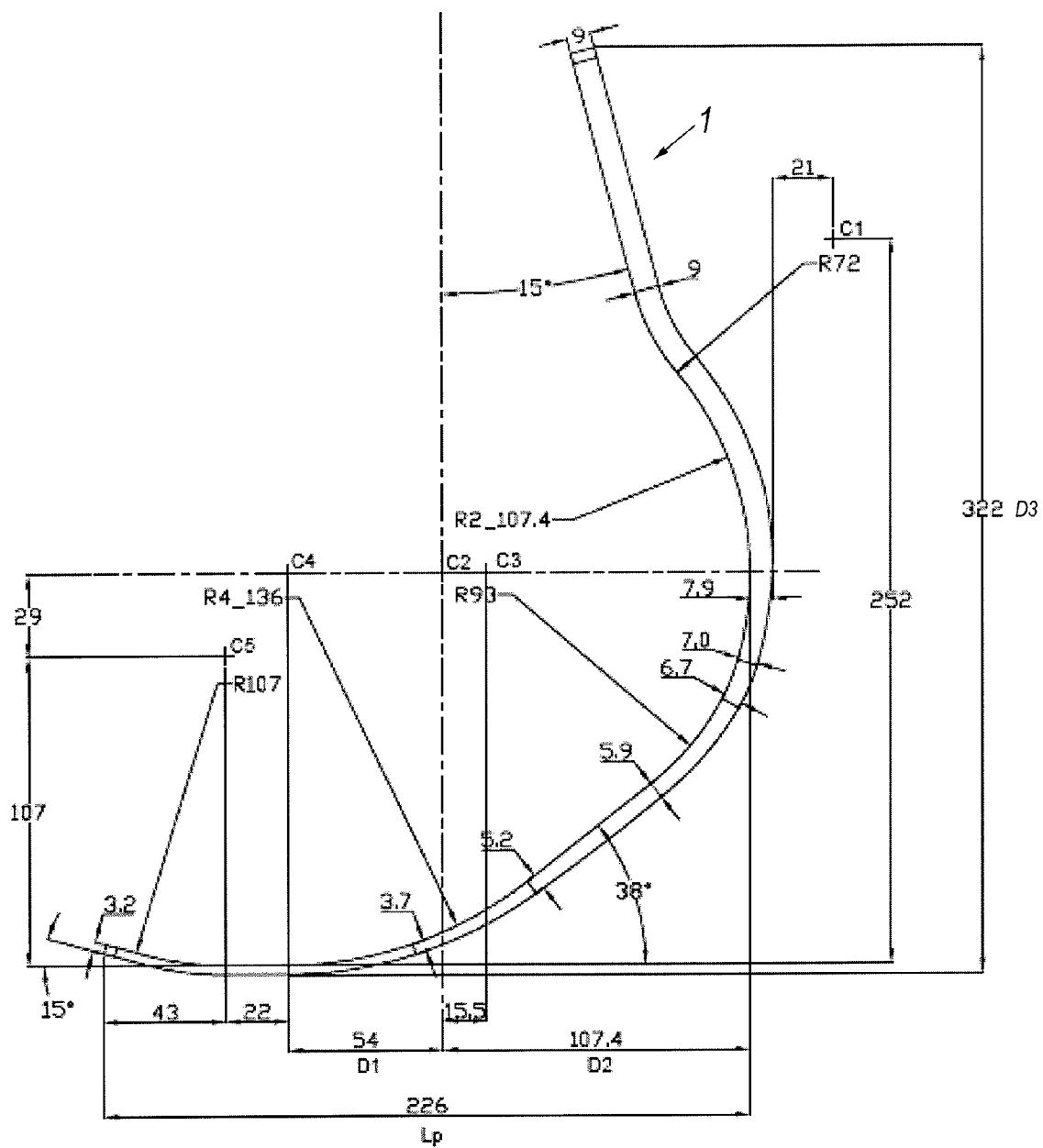

The invention will be more apparent from the ensuing detailed description of one embodiment thereof provided by way of non-limiting example and illustrated in the accompanying drawings, in which:

FIGS. 1 and 4 show the foot (1) of the invention in a configuration using a TT bracket (2), indicated for transtibial user amputation, i.e. below the knee, FIGS. 2 and 3 show the foot (1) of the invention in a configuration using a TF bracket (2a), indicated for transfemoral user amputation, i.e. above the knee, FIG. 5 is a perspective view of the TT bracket (2) for use in fixing the foot in the case of amputations below the knee, as in FIGS. 1 and 4, FIG. 6 is a front view of the TT bracket (2) of FIG. 5, FIG. 7 is a section A-A through the TT bracket (2) of FIG. 2, taken on the sectional plane AA passing through the centre of the frontal plane, FIGS. 8 to 10 are respectively a front, side and horizontal view of a TF bracket (2a) for use in fixing the foot (1) in the case of amputations above the knee as in FIGS. 2 and 3, FIG. 11 is a section A-A through the TF bracket (2a) of FIG. 8, taken on the plane AA passing through the centre of the frontal plane, FIG. 12 shows the different thicknesses of the foot (1) pertaining to class IV, FIGS. 12a, 13 and 14 show variants of the foot (1) of the invention relative to users of different height compared with class IV, as described in detail in FIG. 4, and pertaining respectively to class III, to class II and to class I.

Figure 15:
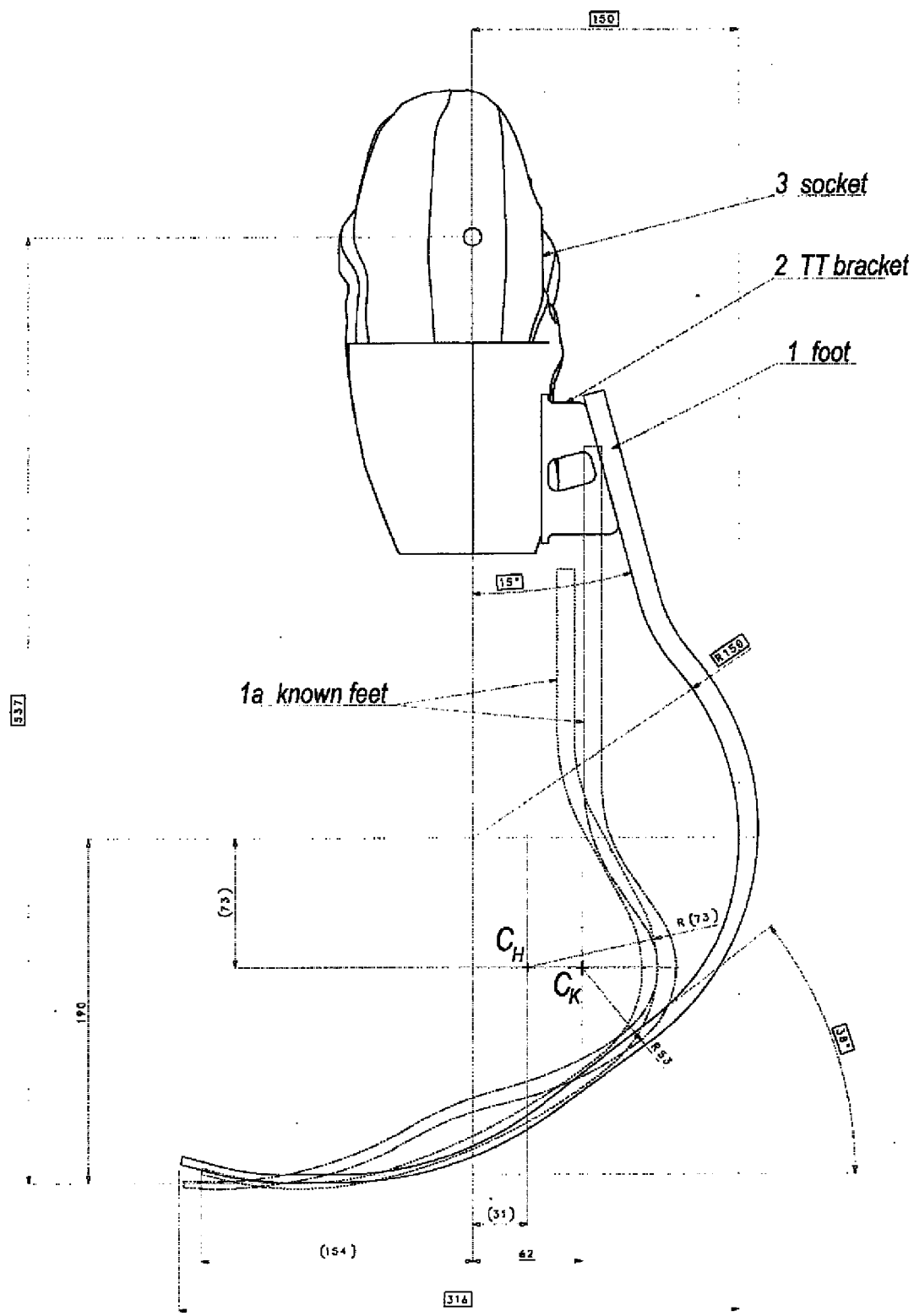

FIG. 15 shows a schematic image of the foot (1) pertaining to class IV, according to the invention, compared with known feet intended for users of the same class.

These figures show a prosthetic foot (1), defined by a J-shaped lamina of composite material which during use, particularly after the loading stage, provides an elastic response which enables the user to advance during running. This foot (1) can be fixed by a TT bracket (2) directly to a socket (3) in the case of transtibial amputations, as shown in FIG. 1, whereas the foot (1) can be fixed to a TF bracket (2a) connectable to a mechanical knee (G) in the case of transfemoral amputations, as shown in FIG. 2.

The mechanical knee (G) is connected to a socket (3a) for subjects with transfemoral amputations.

In the case of transtibial amputations, the TT bracket (2), the socket (3) and the foot (1) of the invention form a transtibial prosthesis, whereas in the case of transfemoral amputations, the foot (12) of the invention, the TF bracket (2a), the mechanical knee (G) and the socket (3a) form a transfemoral prosthesis.

In both solutions, during the static alignment of the prosthesis, this socket (3, 3a) has a main axis (5) passing through a point (4) identifying the femoral epicondyle, real or virtual according to the type of user amputation, and coinciding with the centre of instantaneous rotation of the user's knee during mid-stance.

In the following description, reference will be made to the prosthetic foot (1) in the specific configuration for transtibial amputated subjects, i.e. in the case in which the lower limb has been amputated below the knee. In the case of transfemoral amputated subjects, i.e. above the knee, the foot (1) of the invention is fixed to a TF bracket (2a) which is connected to the socket (3a) via a mechanical knee (G) of known type. In this situation, the femoral epicondyle to which reference is made is virtual and corresponds to the centre of rotation of the mechanical knee during mid-stance, i.e. when the user's femur is perpendicular to the ground.

According to the invention, when the main axis (5) coincides with the loading straight line, during static alignment and during mid-stance, a segment (9) joining a first point (7) of tangency between the foot (1) and the ground line (6) perpendicular to the main axis (5) and a second point (8) of tangency between the foot (1) and a straight line (10) parallel to the main axis, is inclined by an angle α, between 30° and 50°, to the ground line (6) perpendicular to the main axis, said point (8) of tangency lying along a line (11) inclined by an angle β, between 20° and 40°, to said main axis (5), and intersecting said main axis at the point (4).

Preferably, the angle α is 40° and the angle β, is 25°.

When the foot (1) is in contact with the ground line (6) perpendicular to the main axis (%), in the configuration used for mounting the foot onto the socket (3) or onto the mechanical knee (G) during mid-stance, the first point (7) of tangency represents the $5^{th}$ metatarsus of a human foot, the second point (8) of tangency defining the vertex of the curve and the virtual heel of the foot (1) according to the invention.

In particular, in this static foot alignment configuration during mid-stance, the main axis (5) coincides with the loading straight line, the loading straight line meaning that line along which the athlete discharges weight when in the orthostatic position after connecting the prosthesis.

Advantageously, according to the invention, the distance D1 of the first point (7) of tangency from said main axis (5), representative of the distance between the $5^{th}$ metatarsus and the loading straight line, is less than the distance D2 of the second point (8) of tangency from said main axis (5), representative of the distance between the virtual heel and the loading straight line.

Advantageously, the distance D1 is equal to one half of said distance D2.

The prosthetic foot has a length Lp, this length being the distance between the point (8) representative of the virtual heel and the front terminal end or tip (17) of the foot along an axis parallel to the ground line (6), and is equal to 2×D2±20 mm for all classes.

The foot (1), as shown in FIG. 4, comprises a rectilinear first portion (12) for fixing the TT or TF bracket (2 or 2a), and inclined to the main axis (5) by an angle θ between 10° and 20°, preferably 15°.

The foot (1) also comprises:
a curved second portion (13) which defines the morphology of the virtual heel and consists of an upper portion (13a) of radius R2 having its centre of curvature C2 falling on the main axis (5), and a lower portion (13b) of radius of curvature R3 having its centre of curvature at C2;
a third portion (14) defining the foot front and consisting of an upper curved portion (14a) having its centre of curvature C4 positioned at the same distance from the vertex of the heel (8) as the ground line (6) and of radius R4, a curved intermediate portion (14b) of centre of curvature C5 and radius R5, and a lower rectilinear portion (14c) comprising the lower end or tip (17) of the foot (1) and inclined by an angle μ, between 10° and 20°, preferably 15°, to the ground line (6);
a rectilinear fourth portion (15) connecting the curved portion (13) defining the virtual heel to the portion (14) defining the foot front, and being inclined by an angle δ between 30° and 50°, preferably 38°, to the ground line (6);
a curved fifth portion (16) connecting the rectilinear fixing portion (12) to the curved portion (13) defining the virtual heel, and having its centre of curvature at C1 and radius R1.

Some numerical values of those portions forming the foot (1) of the invention will now be indicated for a category of users, the height of whom is between 180 and 190 cm and who take a shoe size between 42 and 45. This user category will be indicated hereinafter as class IV.

For users of different height and foot length, these numerical values which characterise the foot (1) must be divided by a conversion or scale factor related to the ratio between height and length of the human foot.

For example, users of height between 170 and 180 cm and shoe size between 38 and 41 pertain to class III, for whom the foot used will correspond to the numerical values of feet used by users of class IV divided by a factor of 1.1 as indicated in FIG. 12a.

For users pertaining to class II, of height between 160 and 170 cm and shoe size between 34 and 37, the numerical values of class IV are divided by a factor of 1.22 as indicated in FIG. 13.

For users pertaining to class I, of height between 150 and 160 cm and shoe size between 30 and 33, the numerical values of class IV are divided by a factor of 1.366 as indicated in FIG. 14.

The following numerical values apply to users pertaining to class IV, as indicated in FIG. 4:

The radius R1, which generally defines the initial curvature of the foot (1), representative of the human limb of the first portion of the Achilles heel, is equal to 100±2 mm, while C1 is distant from the main axis (5) by 150±50 mm and distant from the ground line (6) by 352±100 mm less the thickness of the foot at its point of contact with the ground.

The radius R2, which defines the virtual heel, is equal to 150±50 mm with its centre of curvature falling on the main axis (5) and a distance from the ground line (6) equal to the distance of the heel vertex (8) from the same ground line (6) less the thickness of the foot at its point of contact with the ground, i.e. 100±65 mm. The centre C2 of the foot (1) of the invention is the centre of the virtual ankle during foot alignment.

As can be seen in FIG. 15, the centres of curvature $C_H$ and $C_K$ of certain known feet $1a$ do not lie on the vertical axis (5) passing through the point (4) indicative of the femoral epicondyle, which is real in the case of transtibial amputations and virtual in the case of transfemoral amputations.

The radius R3, which defines the lower portion of the virtual heel, is of 130±40 mm with its centre of curvature C3 positioned at about 22±7 mm from the loading straight line (5) and 129±22 mm from the vertex (8) of the virtual heel, in contrast to known feet in which this centre of curvature is to the front of the loading straight line.

The portion 15 joining the virtual heel to the virtual foot front is rectilinear, whereas known feet present curved portions, as shown in FIG. 15.

The virtual foot front (14) is defined by:
a first portion (14a) of radius 190±1 mm with centre C4, this point for all foot classes lying on the perpendicular to the ground line (6) passing through the point (7) of tangency to the foot (1) and in the case of class IV lies at 76±22 mm from main axis (5) and at 226±65 mm from the vertex (8) of the heel,
a second portion (14b) of radius R5 of 150±30 mm with centre C5 at 106±30 mm from main axis (5) and at 150±50 mm from the ground line (6),
a rectilinear third portion (14c) terminating with the tip (17) of the foot (1) such that the distance between the point (8) and the extreme tip (17) of the foot (1) is 316 mm from an axis parallel to the ground line (6).

Moreover, as shown in FIG. 1, the width of the class IV foot front H or cross-section of the foot (1), examined in detail, according to the invention is 90±5 mm, i.e. much wider than known feet, such as to ensure equilibrium between the two limbs, i.e. the healthy and the prosthetic, during running. With regard to the other classes the cross-section H is 80±5 mm for class III, 70±5 mm for class II and 60±5 mm for class I.

The points C1, C2, C3, C4 and C5 and their positions are characteristic of all classes of the foot (1), and together with the radii R1, R2, R3, R4, R5 less the scaling factor defining the numerical values of the individual class, they completely define the morphology of the foot (1) of all the different classes.

As shown in FIGS. 1 and 3, the first rectilinear portion 12 is fixed to the rear of the socket (3) by a TT bracket (2) in the transtibial case, shown in FIGS. 5 to 7, and is fixed to a TF bracket (2*a*) in the transfemoral case, shown in FIGS. 8 to 10, itself fixed to the mechanical knee.

Specifically, the first portion of the foot (1), i.e. rectilinear (12), is fixed to the bracket by fixing elements, for example screws.

For example, the TT bracket (2), which is laminated together with the socket (3) to ensure suitable strength of the structure, comprises:
- a flat vertical surface (2, 1) to facilitate its positioning on the socket (3) and hence ensure correct positioning of the foot (1),
- a flat surface (2.2), inclined by 15° to the surface (2.1), on which the foot (1) is positioned and fixed by fixing elements, for example two screws inserted through two holes (2, 3) present in it (FIGS. 5, 6 and 7).

As shown in FIGS. 2 and 3 in the case of transfemoral amputations, the first rectilinear portion (12) of the foot (1) is connected to a TF bracket (2*a*) shown in FIGS. 8, 9 and 10, and is connected to a mechanical knee (G), connected in its turn to the socket (3*a*).

For example, the TF bracket (2*a*) has an upper flat surface (2*a*.1) presenting for example four through holes (2*a*.2) for its fixing by fixing elements, for example screws, to the mechanical knee (G), and a rear flat upper surface (2*a*.3) inclined at 15° to an axis perpendicular to the upper flat surface (2*a*.1); the foot (1) is positioned on the 15°-inclined surface (2*a*.3) and fixed, for example by two screws inserted through two holes (2*a*.4), as shown in FIGS. 8 to 11.

Advantageously according to the invention, the foot (1) is formed by superposing layers of unidirectional carbon/Kevlar fibre fabric and layers of mutually crossing carbon/Kevlar fibre fabric. Each of these layers has a longitudinal elastic traction modulus E of about 116,000 is Mpa and 58,000 Mpa respectively, and an ultimate tensile strength of about 1300 Mpa and 650 Mpa respectively. In particular, the thickness of the foot (1) or rather of the composite material lamina increases starting from a minimum value at the tip (17) of the final rectilinear portion (14*c*) of the foot front (14) to a maximum value at the upper end (18) of the foot (1), as shown in FIG. 4. For example, the foot (1) has eight different thicknesses as shown in FIG. 12: specifically for athletes pertaining to class IV, the lamina has a thickness of 4.5±0.65 mm in the initial region starting from the point (17), and extends along the foot development for 150 mm, the second region of length 20 mm has a thickness of 5.19±0.65 mm, the third region of length 70 mm has a thickness of 7.29±0.65 mm, the fourth region of length 20 mm has a thickness of 8.25±0.65 mm, the fifth region of length 70 mm has a thickness of 9.38±0.65 mm, the sixth region of length 33 mm has a thickness of 9.8±0.65 mm, the last two regions are measured from the upper end (18) of the foot (1), at 447 mm from the ground line (6), with the seventh region having a thickness of 12 mm±0.65 mm and a length of 120 mm from an axis parallel to the main axis (5) and the eighth region having a thickness of 10 mm±0.65 mm and a length of 20 mm from an axis parallel to the main axis (5).

For athletes pertaining to the other classes, the thickness in the individual regions is calculated by dividing by the scaling factor, which is 1.1 in the case of class III, 1.2 in the case of class II and 1.366 in the case of class I, as shown in FIGS. 12*a*, 13, 14 with a tolerance of 0.65 mm. In practice, the foot thickness increases for all classes from one region to another, starting from the tip (17), where it has its minimum value, to the upper end (18), where it has its maximum value, by a factor for adjacent regions which is between 1.02 and 1.40; the ratio between the foot thickness at the tip (17) and at the upper end (18) is 2.7±0.2 for all classes.

Three sub-classes are provided within each foot class based on the weight of the user, these sub-classes varying in terms of different thickness: in this respect the strength and the elastic response of the foot (1) are in relation to the load applied to it, which is a function of the weight of the user.

A description will now be given of the method for fixing the foot (1) to the TT bracket (2) and to the socket (3) in the case of transtibial users and for fixing the foot (1) to the TF bracket (2*a*) and to the mechanical knee (G) in the case of transfemoral users, and for achieving the relative static alignment of the foot (1) to the main axis (5), which is done by an orthopaedic technician.

Specifically, the foot (1) is positioned in proximity to the TT bracket (2) and to the socket (3) worn by the user in an orthostatic position, with provisional fixing and positioning.

Based on this initial positioning of the bracket on the socket, the TT bracket (2) is fixed onto the socket (3) with glue.

Advantageously, during static alignment the TT bracket (2) is positioned with its flat vertical surface (2.1) adhering to the socket (3) and fixed, as already stated, by glue such that the flat surface (2.2) of the TT bracket (2) on which the foot (1) is to be fixed will have an inclination of 15° to the main axis (5) passing through the point (4) identifying the real femoral epicondyle. The TT bracket (2) is then laminated with the socket such that they become a single structure.

In the case of class IV, which comprises users of height between 180 and 190 cm, the foot (1), rigid with the TT bracket (2), once fixed by fixing elements, for example two screws, must be positioned together with the TT bracket (2) on the socket (3), such that the upper end (18) of the foot (1) is at a distance D3 from the ground line (6) of 440±10 mm, for example 447 mm and hence at about 100±40 mm from the point (4), and at a distance D4 from the main axis (5) and loading straight line of 65±5 mm. The fixing point for the foot (1) has been established such as to enable the functionality of the prosthetic foot (1) to approach that of the human foot, in which the Achilles tendon, for class IV users, lies at about 100 mm below the centre of the popliteal cavity formed by the union of the Gastrocnem and Soleum muscles, and is responsible for 90% of the foot elasticity.

For the other foot classes, III, II and I, alignment is done in the same manner, but the distance D3 of the upper end (18) of the foot (1) from the ground line (6) and the distance D4 of the upper free end (18) from the main axis vary by the scaling factor: D3 becomes equal to 410±20 mm, for example 416 mm for class III, 360±30 mm, for example 365 mm for class II, and 320±10 mm, for example 322 mm for class I, and D4 becomes 59±5 mm for class III, 53±5 mm for class II, and 49±4 mm for class I.

In the case of transfemoral amputations, the foot (1) of the invention is fixed to the TF bracket (2*a*) which itself is fixed to the mechanical knee (G) by fixing elements, for example four screws.

In this case, the foot (1) is fixed by the following steps:
- fixing the mechanical knee (G) to the socket (3*a*) worn by the user in an orthostatic position,
- fixing the TF bracket (2*a*) to the mechanical knee (G) by fixing elements, for example four screws,
- fixing the foot (1) to the TF bracket (2*a*) such that, for class IV users, the upper end (18) of the foot is at a distance D3 from the ground line (6) of 440±10 mm, for example 447 mm and hence at about 100±40 mm from the point (4), in this case the virtual femoral epicondyle and centre of rotation of the mechanical knee being in mid-stance and at a distance D4 from the main axis (5) and loading straight line of 65±5 mm.

As in the case of transtibial users, for the other foot classes III, II and I of transfemoral users, the alignment is done in the same manner, but the distance D3 of the upper end (18) of the foot (1) from the ground line (6) and the distance D4 of the upper end (18) from the main axis vary by the scaling factor: D3 becomes equal to 410±20 mm, for example 416 mm for class III, 360±30 mm, for example 365 mm for class II, and 320±10 mm, for example 322 mm for class I, and D4 becomes 59±5 mm for class III, 53±5 mm for class II, and 49±4 mm for class I.

Consequently the foot (1) of the invention presents a segment (11) with a predetermined inclination between the point (4) and the vertex (8) of the virtual heel of 30°±5° to the main axis (5), and a segment (9) with an inclination of 40°±5° between the point of tangency (7) indicative of the 5$^{th}$ metatarsus and the vertex (8) of the virtual heel, such as to best simulate the plantar flexure of the human foot which in the case of normal athletes is of 40°.

Advantageously, these effects are best obtained if the first rectilinear portion (12) of the foot (1) is inclined by 15° to the main axis (5).

As can be seen from FIG. 15, these characteristics are not present in feet of known type.

In conclusion, the foot (1) of the invention results in smoother running biomechanics, enabling the expert athlete to achieve better performance in sporting competitions, and enabling the beginner to more easily initiate a sporting career as the foot (1) of the new invention minimizes the energy consumed in running and hence the user fatigue.

It therefore provides the following advantages:
  it does not present the negative force component in the advancement direction (Figure) presented by feet of known type, which implies greater muscular work for the hip joint by the user;
  the horizontal force (Figure) responsible for advancement, which the foot (1) of the new invention is able to develop after loading, is increased by 15% over known feet;
  during contact between the foot (1) and the ground, the moment in which the horizontal force (Figure) reverses from absorbent to propulsive, is immediately after mid-stance, i.e. immediately after the moment in which the femur is perpendicular to the ground, to enable the user to utilize to a maximum the elastic response of the foot (1);
  the vertical force (Fz) is greater by 15% than known feet;
  during contact between the foot (1) and the ground, the moment in which the vertical force (Fz) is a maximum is immediately after mid-stance, to enable the user to utilize to a maximum the elastic response of the foot (1);
  the modulus ratio between the vertical force (Fz) and the horizontal force (Fx) is modified in favour of Fx, such as to facilitate advancement during running, with a knee trajectory closer to the ground.

The figures show a number of numerical dimensions, which are to be considered as examples only.

The invention claimed is:

1. A prosthetic foot (1) in the form of a composite material lamina with a characteristic J-shape, fixable by a TT bracket (2) directly to a socket (3) containing the stump, i.e. the residual part of the amputated lower limb, in the case of users with transtibial amputations, or fixable by a TF bracket (2a) to a mechanical knee (G), itself fixable to a socket (3a), in the case of users with transfemoral amputations, said socket (3 or 3a) having a main axis (5) which coincides with the loading straight line during static alignment and during mid-stance, said loading straight line being that along which the user, after applying the prosthesis, discharges body weight in the static position,
  the main axis (5) passing through a point (4) identifying the femoral epicondyle, real in the case of transtibial users and virtual and representative of the centre of rotation of the mechanical knee (G) during mid-stance in the case of trans femoral users, said foot being characterised by comprising:
  a curved second portion (13) which defines the morphology of the virtual heel and consists of an upper portion (13a) having its centre of curvature falling on the main axis (5), and a lower portion (13b);
  a third portion (14) defining the foot front and consisting of an upper curved portion (14a) having a centre of curvature positioned at the same distance from the ground line (6) as the centre of curvature of the portion (13a), a curved intermediate portion (14b) comprising the lower end or tip (17) of the foot (1) and inclined by an angle $\mu$ of between 10° and 20° to the ground line (6);
  a rectilinear fourth portion (15) connecting the curved portion (13) defining the virtual heel to the portion (14) defining the foot front, and being inclined by an angle $\delta$ of between 30° and 50° to the ground line (6) and further characterised by having a morphology such that:
  a straight line (9) joining the point (7), representative of the 5$^{th}$ virtual metatarsus and being a point of tangency between said foot (1) and the ground line (6) perpendicular to the main axis (5), to the point (8), representative of the virtual heel and being a point of tangency between the foot (1) and a straight line (10) parallel to the main axis (5), is inclined by an angle $\alpha$ of between 30° and 50° to the ground line (6),
  and in that
  the point (8), representative of the virtual heel, lies along a line inclined by an angle $\beta$ of between 20° and 40° to said main axis (5) and intersects the main axis at a point representative of the real or virtual femoral epicondyle (4).

2. The prosthetic foot (1) of claim 1, characterised in that said angle $\alpha$ is 40° and said angle $\beta$ is 25°.

3. The prosthetic foot (1) of claim 1, characterised in that the distance D1 of the point (7) of tangency, representative of the 5$^{th}$ metatarsus, from said main axis (5), is less than the distance D2 of the point (8) of tangency, representative of the 5$^{th}$ virtual metatarsus, from said main axis (5).

4. The prosthetic foot (1) of claim 1, characterised in that the distance D1 is equal to one half of said distance D2.

5. The prosthetic foot (1) of claim 1, characterised by comprising a first rectilinear portion (12) inclined to said main axis (5) by an angle $c$ of between 10° and 20°.

6. The prosthetic foot (1) of claim 5, characterised in that the first rectilinear portion (12) is fixed to the TT bracket (2) or to the TF bracket (2a), depending on the type of user amputation, said bracket being itself fixed to the socket (3) in the case of transtibial amputation or to the mechanical knee (G) in the case of transfemoral amputation.

7. The prosthetic foot (1) claim 1, characterised in that said angle $c$ is 15°.

8. The prosthetic foot (1) of claim 1, characterised in that said angle $\mu$ is 15° and said angle $\delta$ is 38°.

9. The prosthetic foot (1) of claim 1, characterised by being formed by superposing layers of unidirectional carbon/Kevlar fibre fabric and layers of mutually crossing carbon/Kevlar fibre fabric.

10. The prosthetic foot (1) of claim 1, characterised by its thickness increasing for all classes from one region to another, starting from the tip (17), where it has its minimum value, to the upper end (18), where it has its maximum value, by a factor for adjacent regions which is between 1.02 and 1.40; while the ratio between the foot thickness at the tip (17) and at the upper end (18) is 2.7±0.2 for all classes.

11. The prosthetic foot (1) of claim 1, characterised by being selected from three sub-classes within each foot class, based on the weight of the user, these sub-classes varying in terms of different thickness: in this respect the strength and the elastic response of the foot (1) are in relation to the load applied to it, which is a function of the weight of the user.

12. The prosthetic foot (1) of claim 1, characterised by having a length Lp, this length being the distance between the point (8) representative of the virtual heel and the tip (17) of the foot (1) along an axis parallel to the ground line (6), of 2×D2±20 mm, where D2 is the shortest distance from the point (8) representative of the virtual heel and the main axis 5.

* * * * *